United States Patent
LLoyd et al.

(10) Patent No.: US 12,330,022 B2
(45) Date of Patent: Jun. 17, 2025

(54) REHABILITATION SYSTEM

(71) Applicant: Griffith University, Nathan (AU)

(72) Inventors: David Gavin LLoyd, Queensland (AU); Claudio Pizzolato, Queensland (AU); Dinesh Palipana, Queensland (AU); David John Saxby, Queensland (AU); Laura Elizabeth Diamond, Queensland (AU)

(73) Assignee: Griffith University, Nathan (AU)

( * ) Notice: Subject to any disclaimer, the term of this patent is extended or adjusted under 35 U.S.C. 154(b) by 478 days.

(21) Appl. No.: 17/614,208

(22) PCT Filed: Jun. 4, 2020

(86) PCT No.: PCT/AU2020/050566
§ 371 (c)(1),
(2) Date: Nov. 24, 2021

(87) PCT Pub. No.: WO2020/243781
PCT Pub. Date: Dec. 10, 2020

(65) Prior Publication Data
US 2022/0249907 A1 Aug. 11, 2022

(30) Foreign Application Priority Data
Jun. 4, 2019 (AU) .............................. 2019901921

(51) Int. Cl.
*A63B 24/00* (2006.01)
*A61N 1/36* (2006.01)
(Continued)

(52) U.S. Cl.
CPC ...... *A63B 24/0062* (2013.01); *A61N 1/36003* (2013.01); *A61N 1/36031* (2017.08);
(Continued)

(58) Field of Classification Search
CPC ............ A63B 24/0062; A63B 22/0605; A63B 71/0622; A63B 2022/0094;
(Continued)

(56) References Cited

U.S. PATENT DOCUMENTS 6,152,855 A * 11/2000 Dean, Jr. .............. A61H 1/0262
601/24
8,249,714 B1 8/2012 Hartman et al.
(Continued)

FOREIGN PATENT DOCUMENTS

CN 101961527 A 2/2011
CN 102579229 A 7/2012
(Continued)

OTHER PUBLICATIONS

Office Action date Dec. 5, 2023, 13 pages, received in corresponding Japanese patent application No. 2021-572105.
(Continued)

*Primary Examiner* — Jonathan T Kuo
(74) *Attorney, Agent, or Firm* — BLANK ROME LLP

(57) ABSTRACT

The present invention relates to a rehabilitation system for rehabilitating a person with a neurological condition, such as a spinal cord injury (SCI). The system includes exercise equipment for enabling the person to exercise. One or more sensors are provided for sensing information from the person during exercise. The system also includes a model of the exercising person configured to receive the sensed information from the sensors and generate electrical stimulation for the person. Advantageously, the personalized computer model may be used to generate suitable electrical stimulation for the person, and avoid excessive stresses on the person which can lead to the fracturing of bones.

18 Claims, 1 Drawing Sheet

(51) Int. Cl.

| | | |
|---|---|---|
| *A63B 22/00* | (2006.01) | |
| *A63B 22/06* | (2006.01) | |
| *A63B 71/06* | (2006.01) | |
| *G06F 3/01* | (2006.01) | |
| *G16H 20/30* | (2018.01) | |
| *G16H 40/67* | (2018.01) | |

(52) U.S. Cl.
CPC ...... *A63B 22/0605* (2013.01); *A63B 71/0622* (2013.01); *G06F 3/015* (2013.01); *G16H 20/30* (2018.01); *G16H 40/67* (2018.01); *A63B 2022/0094* (2013.01); *A63B 2022/0652* (2013.01); *A63B 2071/0625* (2013.01); *A63B 2071/0638* (2013.01); *A63B 2071/0655* (2013.01); *A63B 2071/0666* (2013.01); *A63B 2213/004* (2013.01); *A63B 2220/30* (2013.01); *A63B 2220/54* (2013.01); *A63B 2220/836* (2013.01)

(58) Field of Classification Search
CPC .... A63B 2022/0652; A63B 2071/0625; A63B 2071/0638; A63B 2071/0655; A63B 2071/0666; A63B 2213/004; A63B 2220/30; A63B 2220/54; A63B 2220/836; A63B 21/00178; A63B 21/0059; A63B 2071/0018; A63B 2220/80; A63B 2230/04; A63B 2230/06; A63B 2230/10; A63B 2230/40; A61N 1/36003; A61N 1/36031; A61N 1/0452; A61N 1/0551; A61N 1/36062; A61N 1/36139; G06F 3/015; G06F 3/011; G06F 3/012; G16H 20/30; G16H 40/67; A61B 5/0205; A61B 5/0245; A61B 5/08; A61B 5/163; A61B 5/316; A61B 5/318; A61B 5/369; A61B 5/389; A61B 5/681; A61B 5/346; A61B 5/372; A61B 5/397; A61B 5/150809; A61B 5/150816; A61B 5/150824; A61B 5/4836; A61B 5/486; A61B 5/6803; A61B 5/7264; A61B 2505/09; A61B 2562/0219; A61B 2562/0247; G06T 19/006

See application file for complete search history.

(56) References Cited

U.S. PATENT DOCUMENTS

| | | | |
|---|---|---|---|
| 9,808,621 B2* | 11/2017 | Kelly | A61B 5/291 |
| 10,130,311 B1* | 11/2018 | De Sapio | A61B 5/7455 |
| 2004/0172093 A1 | 9/2004 | Rummerfield | |
| 2006/0165756 A1 | 7/2006 | Catani et al. | |
| 2006/0199700 A1 | 9/2006 | LaStayo et al. | |
| 2007/0179534 A1 | 8/2007 | Firlik et al. | |
| 2013/0053734 A1 | 2/2013 | Barriskill et al. | |
| 2014/0005743 A1 | 1/2014 | Giuffrida et al. | |
| 2014/0277582 A1 | 9/2014 | Leuthardt et al. | |
| 2016/0235323 A1* | 8/2016 | Tadi | A61B 5/0006 |
| 2017/0036022 A1* | 2/2017 | Kelly | A61B 5/375 |
| 2018/0036531 A1 | 2/2018 | Schwarz et al. | |
| 2018/0333575 A1* | 11/2018 | Bouton | A61B 5/726 |

FOREIGN PATENT DOCUMENTS

| | | |
|---|---|---|
| CN | 102727361 A | 10/2012 |
| CN | 106492347 A | 3/2017 |
| CN | 106994013 A | 8/2017 |
| JP | 2009512516 A | 3/2009 |
| JP | 2018-139975 | 9/2018 |
| JP | 2018-139975 A | 9/2018 |
| WO | WO 2014/153201 A1 | 9/2014 |
| WO | WO 2015/152122 A1 | 10/2015 |
| WO | WO 2018/033591 A2 | 2/2018 |
| WO | WO 2018/154042 A1 | 8/2018 |

OTHER PUBLICATIONS

Simao Brito da Luz et al., "Feasibility of using MRIs to create subject-specific parallel-mechanism joint models," *Journal of Biomechanics*, 53 (2017) pp. 45-55.

Claudio Pizzolato et al., "Finding the sweet spot via personalised Achilles tendon training: the future is within reach," *Br J. Sports Med*, Jan. 2019, vol. 53, No. 1.

Claudio Pizzolato et al., "Bioinspired Technologies to Connect Musculoskeletal Mechanobiology to the Person for Training and Rehabilitation," *Frontiers in computational Neuroscience Review*, published: Oct. 2017 | vol. 11 | Article 96, pp. 1-16.

C. Pizzolato et al., "Real-time inverse kinematics and inverse dynamics for lower limb appli-cations using OpenSim" *Computer Methods in Biomechanics and Biomedical Engineering*, 2017, vol. 20, No. 4, pp. 436-445, http://dx.doi.org/10.1080/10255842.2016.1240789.

Rubia van den Brand et al., "Restoring Voluntary Control of Locomotion after Paralyzing Spinal Cord Injury," *Science*, Jun. 1, 2012 vol. 336, pp. 1182-1186.

Yury P. Gerasimenko et al., "Noninvasive Reactivation of Motor Descending Control after Paralysis," *Journal of Neurotrauma* 32:1968-1980 (Dec. 15, 2015).

Dimitry G. Sayenko et al., "Self-Assisted Standing Enabled by Non-Invasive Spinal Stimulation after Spinal Cord Injury," *Journal of Neurotrauma* 36:1435-1450 (May 1, 2019).

Megan L. Gill, "Neuromodulation of lumbosacral spinal networks enables independent stepping after complete paraplegia," *Nature Medicine*, vol. 24, Nov. 2018, 1677-1682.

Claudia A. Angeli et al., "Recovery of Over-Ground Walking after Chronic Motor Complete Spinal Cord Injury," N Engl J Med 379;13, Sep. 27, 2018, pp. 1244-1250.

Donati, A. R. C. et al., "Long-Term Training with a Brain-Machine Interface-Based Gait Protocol Induces Partial Neurological Recovery in Paraplegic Patients," *Sci. Rep.*, 6, 30383; 2016, pp. 1-16.

The extended European search report, mailed date May 11, 2023, 9 pages, received in corresponding EP application No. 20817609.9.

First Office Action dated Jun. 7, 2024 issued on corresponding Chinese Patent Application No. 202080041275.3.

Notification of Reasons for Rejection dated Dec. 5, 2023 issued on corresponding Japanese Patent Application No. 2021-572105.

First Written Opinion dated Oct. 30, 2023 issued in corresponding Singapore Patent Application No. 11202113224X.

Examination Report issued in Australian Patent Application No. 2020287071 dated Oct. 30, 2024.

* cited by examiner

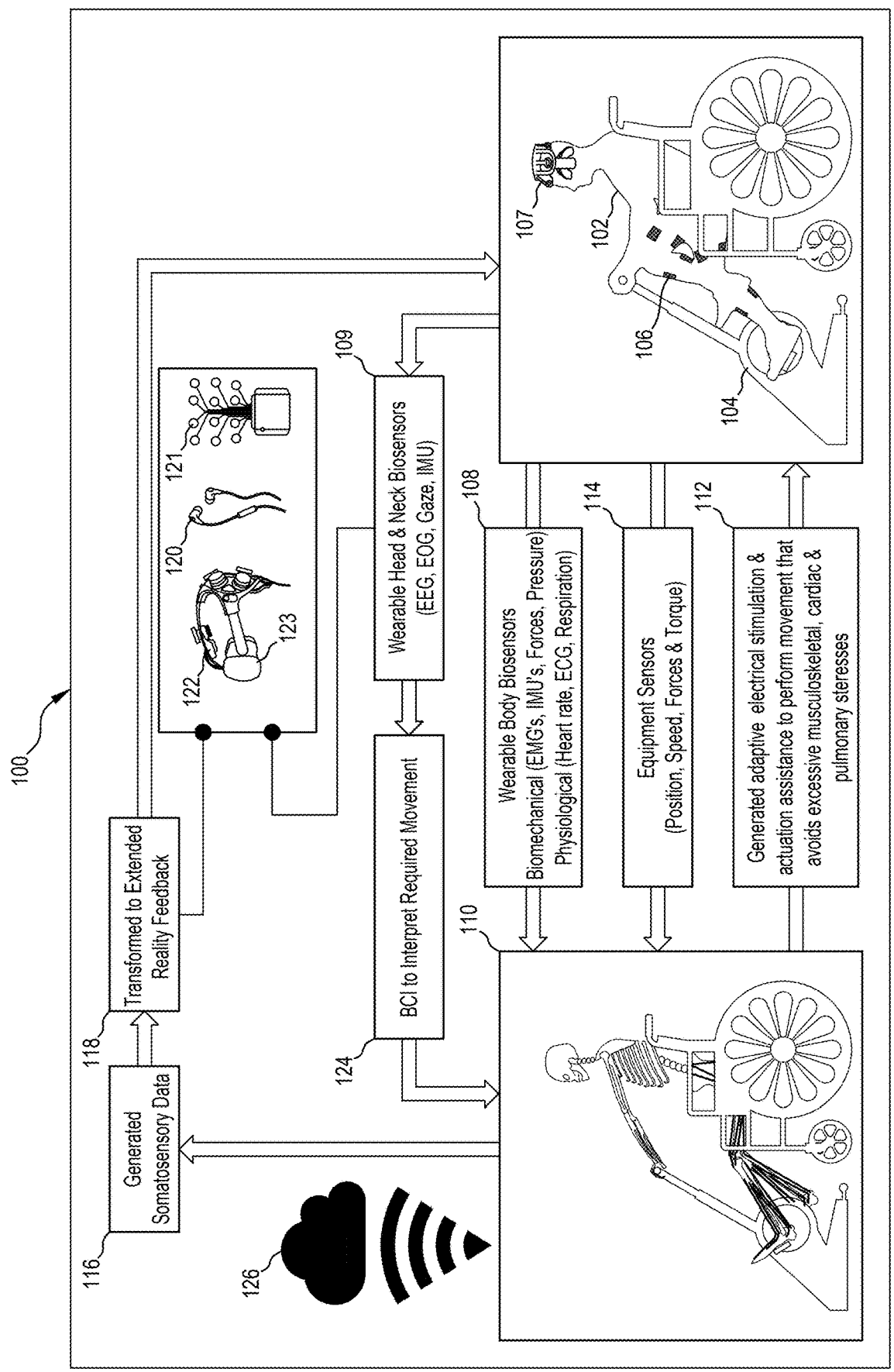

REHABILITATION SYSTEM

This application is a U.S. National Stage Application of International Application No. PCT/AU2020/050566, filed on Jun. 4, 2020, which claims priority to Australian Application No. 2019901921, filed on Jun. 4, 2019, both of which are hereby incorporated herein by reference in their entirety.

TECHNICAL FIELD

The present invention generally relates to a neurorehabilitation system for a person with an acquired or developmental neurological condition such as spinal cord injury, brain injury, cerebral palsy, or spasticity. The preferred embodiment of the invention will be presented for application to spinal cord injury (SCI).

BACKGROUND

The reference to any prior art in this specification is not, and should not be taken as an acknowledgement or any form of suggestion that the prior art forms part of the common general knowledge.

For thousands of years SCI was thought to be irreversible. This view is now changing. Recent scientific evidence has shown that thought-controlled rehabilitation robots can restore some voluntary movement in SCI. Further evidence suggests that providing motor sensory feedback can restore damaged spinal pathways.

Other studies have also shown that electrically stimulating spinal cord or muscles can help. However, such stimulation has been known to activate muscles to fracture bones that have been weakened through non-use over time.

Further studies have shown that rehabilitation using motor-driven exoskeletons can help regain voluntary movement in SCI. Since the motors, and not the stimulated muscles' activation, generate the SCI patient's movement this form of rehabilitation can protect against over loading. However, motor-driven rehabilitation does not facilitate use of stimulated muscle activation and action to generate movement, as enabled by electrical stimulation.

Numerous studies have also explored the use of biofeedback in rehabilitation, using visual, haptic, or auditory monitors to provide information to the user and improve their training. Commonly this involves directly providing visual information regarding joint angles or body position. However, our brain does not directly receive information regarding the position of our joints during movement, instead it subconsciously interprets the electrical signals from mechanical sensors in our muscles and tendons (i.e. muscle spindles and golgi tendon organs, respectively), which generate electrical signals that are associated with length, velocity and tension of the muscles in which the sensors are embedded.

The use of all mentioned methods for SCI rehabilitation can be complex and need considerable training. Health professionals are therefore reticent to use these approaches, relying on more time-consuming and less effective hands-on rehabilitation methods.

The preferred embodiment provides an improved rehabilitation system for rehabilitating a person with a SCI. The preferred system integrates all aforementioned aspects of rehabilitation to help safely regain voluntary movement in SCI. Furthermore, the preferred system, through careful design and use of computer modelling will facilitate the systems ease of use in a clinical setting.

SUMMARY OF THE INVENTION

According to one aspect of the present invention, there is provided a rehabilitation system for rehabilitating a person with a neurological condition, the system including:
  exercise equipment for enabling the person to exercise;
  a human machine interface with one or more sensors for sensing information from the person's head, neck and body during exercise;
  a human machine interface that has somatosensory feedback enabled by visual feedback, preferably via virtual/augmented reality, tactile via haptic feedback, or auditory by ear phones;
  a personalized computer model of the exercising person on the exercise equipment configured to receive the information flow from the sensors and generate functional or spinal cord electrical stimulation and motorised assistance, for the person; and
  a personalized computer model that is able to synthesize and generate somatosensory feedback.

According to another aspect of the present invention, there is provided a rehabilitation system for rehabilitating a person with a neurological condition, the system including:
  exercise equipment for enabling the person to exercise;
  one or more sensors for sensing information from the person during exercise; and
  a model of the exercising person configured to receive the sensed information from the sensors and generate (functional or spinal cord) electrical stimulation for the person.

Advantageously, the personalized computer model may be used to generate suitable functional or spinal cord electrical stimulation for the person, and avoid excessive stresses on the person which can lead to the fracturing of bones.

The personalized computer model may include a neuromusculoskeletal model.

The sensors may include biomechanical and/or physiological biosensors on the person's head, neck and/or body. The sensed information may relate to any one or more of electromyography (EMG), inertial measurement units, electroencephalography (EEG), electrooculography (EOG), eye gaze, heart rate, electrocardiography (ECG), and respiration.

The sensors may include wearable sensors worn by the person.

The exercise equipment may include a recumbent ergometer, upper-arm ergometer or articulated system, rowing system, or walking system. The system may further include an actuator(s) to assist the person to perform the exercise on the equipment. The actuator may include a motor.

The sensors may further include one or more equipment sensors for sensing information of the equipment that is also provided to the model for generating the functional or spinal cord electrical stimulation, and/or actuation assistance. The equipment sensors may include speed, motor current, force and/or torque sensors.

The model may be configured to be a human machine interface (HMI) between the person and equipment. The HMI my include a headset, in turn, including an EEG system that will provide data to the brain computer interface (BCI) model to classify the person's exercise intention and intensity. The intent and intensity may trigger the model to generate functional or spinal cord electrical stimulation and actuation assistance to enable the person to perform the desired exercise on the equipment.

The model may be further configured to generate sensory data to be feedback to the person via the HMI. The sensory data may include somatosensory, cardiac and/or respiratory data. Sensory data may be provided to person by visual, auditory and/or intact haptic feedback pathways. The HMI headset may provide these extended reality feedback by including virtual or augmented reality, or via ear phones and/or haptic devices.

According to another aspect of the present invention, there is provided a rehabilitation method for rehabilitating a person with a neurological condition, the method including:
exercising the person with exercise equipment;
sensing information from the exercising person and exercise equipment; and
receiving the sensed information and generating functional electrical stimulation and actuator assistance for the person using a model of the exercising person using the exercise equipment.

Any of the features described herein can be combined in any combination with any one or more of the other features described herein within the scope of the invention.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to drawing as follows:

FIG. 1 is a schematic view of a rehabilitation system in accordance with an embodiment of the present invention.

DETAILED DESCRIPTION OF PREFERRED EMBODIMENTS

According to an embodiment of the present invention, there is provided a rehabilitation system 100 for rehabilitating a person 102 with a SCI. The system 100 includes exercise equipment 104, maybe in the form of a recumbent cycle or ergometer, which enables the person 102 to exercise. Personal wearable head, neck and body biosensors 106 and 107 (biomechanical and physiological biosensors) are provided for sensing personal information 108 and 109 from the person 102 during exercise.

The system 100 further includes a personalized computer model 110 of the exercising person 102 on the exercise equipment 104 for receiving the sensed personal information 108 and 109 from the sensors 106 and 107 and generating electrical stimulation and actuation assistance 112 for the person. Advantageously, the personalized model 110 is used in generating suitable adaptive electrical stimulation for the person 102, and avoids excessive musculoskeletal, cardiac and pulmonary stresses on the person 102 as well as the potential fracturing of bones.

The rehabilitation system 100 further includes equipment sensors (e.g. speed, torque, etc.) for sensing equipment information 114 of the equipment 104. The equipment information 114 is also provided to the model 110 and used in generating the electrical stimulation and actuation assistance 112.

The model 110 is configured to generate sensory data 116 to be provided to the person 102 through extended reality feedback 118 in the HMI 119. The extended reality 118 in HMI 119 includes a virtual or augmented reality headset 122 with visual 123, auditory 120 and tactile feedback 121. The HMI 119 will employ a brain computer interface (BCI) 124 that may use EEG, EOG, eye gaze sensor data 109 in the headset 122 worn by the person 102. The model 110 is also configured to receive data from the BCI 124 that is the interpretation of the person's required movement when the person 102 thinks about an action. The model 110 is typically stored in the cloud 126 and IoT enabled.

The functionality of the system 100 is now described in greater detail below.

The neuromusculoskeletal model 110 incorporates a Digital Twin, which is a computer representation of the person's bones, muscles, joints, and nervous system. The Digital Twin technology is used in real-time to virtually bypass the site of SCI, again connecting sensory and motor pathways between brain, spinal cord, and muscles.

The model 110 includes BioSpine, which is an innovative application of Digital Twin technology through the HMI headset 122 that is combined with virtual/augmented reality 123, auditory 120 and haptic devices 121, and biosensors 106 and 107. BioSpine integrates a unique set of intelligent rehabilitation assistive technologies controlled by the Digital Twin to restore the interrupted motor and sensory connections in the spine. BioSpine integrates the following discrete technologies into the seamless system 100: HMI 119, wearable biosensors 106 and 107, electrical stimulation 112 of lower limb muscles of the person 102, motor-assisted leg cycling in the case presented, augmented somatosensory signals 116 transformed extended reality 118 with visual 123, auditory 120 and haptic 121 biofeedback.

The system 100 is intuitively and automatically controlled by the personalised Digital Twin of the patient 102.

Personalised Digital Twins of each participant 102 can be developed combining magnetic resonance imaging (MRI) [2] and artificial intelligence methods. Electroencephalograms (EEG) can be captured via a portable wireless headset (e.g. Wearable Sensing DSI7 or DSI-VR300, Switzerland) 122 and processed in the BCI 124 using AI methods to discriminate whether the patient wishes to perform, and how intensely they wish to do, in this example case, the cycling exercise.

In the example case of cycling, the patient's motor intention to cycle data 124 will control the Digital Twin, which in turn will optimally stimulate muscles via electrical stimulation 112 and provide appropriate motorised assistance 112 to achieve cycling. Importantly, the Digital Twin coordinates the electrical stimulation 112 and motorised assistance 112 to ensure that stimulated muscle activation assists, rather than opposes, the motorised actuation to perform the movement. Biomechanical and physiological information 108 from multiple wearable biosensors 106 (e.g., electromyography, inertial measurement units, heart rate, electrocardiogram, and respiration) can be interpreted by the patient's Digital Twin to progressively adapt the amount of ergometer pedal-assistance in order to maximally engage the patient 102, while also maintaining musculoskeletal tissue loads and cardiovascular demand within safe levels [3, 4].

Finally, the patient's Digital Twin can synthesise somatosensory information 116 that will be redirected to higher somatosensory areas via extended reality 118, visual 123, auditory 120 and/or haptic 121 feedback [4, 5].

Off-the-shelf known pharmacological adjuncts (e.g., buspirone) with an established safety profile utilised in prior studies [6-10] can be added to measure their additive effect on neural plasticity. The system 100 is designed to retrofit and update existing, commercially available equipment 104.

A person skilled in the art will appreciate that many embodiments and variations can be made without departing from the ambit of the present invention.

The system 100 may further include an actuator, such as a robotic motor coupled to the drive crank, for actuating the exercise equipment 104. In use, the model 110 actuates the actuator to some extent to assist the person 102.

In compliance with the statute, the invention has been described in language more or less specific to structural or methodical features. It is to be understood that the invention is not limited to specific features shown or described since the means herein described comprises preferred forms of putting the invention into effect.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

REFERENCES

1. [Intentionally left blank]2. Brito da Luz S, Modenese L, Sancisi N, Mills P M, Kennedy B, Beck B R, et al. Feasibility of using MRIs to create subject-specific parallel-mechanism joint models. J Biomech 2017; 53: 45-55.
3. Pizzolato C, Lloyd D G, Zheng M H, Besier T F, Shim V B, Obst S J, et al. Finding the sweet spot via personalised Achilles tendon training: the future is within reach. British Journal of Sports Medicine 2019; 53: 11-12.
4. Pizzolato C, Lloyd D G, Barrett R S, Cook J L, Zheng M H, Besier T F, et al. Bioinspired Technologies to Connect Musculoskeletal Mechanobiology to the Person for Training and Rehabilitation. Front Comput Neurosci 2017; 11: 96.
5. Pizzolato C, Reggiani M, Modenese L, Lloyd D G. Real-time inverse kinematics and inverse dynamics for lower limb applications using OpenSim. Comput Methods Biomech Biomed Engin 2017; 20: 436-445.
6. van den Brand R, Heutschi J, Barraud Q, DiGiovanna J, Bartholdi K, Huerlimann M, et al. Restoring voluntary control of locomotion after paralyzing spinal cord injury. Science 2012; 336: 1182-1185.
7. Gerasimenko Y P, Lu D C, Modaber M, Zdunowski S, Gad P, Sayenko D G, et al. Noninvasive Reactivation of Motor Descending Control after Paralysis. J Neurotrauma 2015; 32: 1968-1980.
8. Sayenko D, Rath M, Ferguson A R, Burdick J, Havton L, Edgerton V R P D, et al. Self-assisted standing enabled by non-invasive spinal stimulation after spinal cord injury. J Neurotrauma 2018.
9. Gill M L, Grahn P J, Calvert J S, Linde M B, Lavrov I A, Strommen J A, et al. Neuromodulation of lumbosacral spinal networks enables independent stepping after complete paraplegia. Nat Med 2018; 24: 1677-1682.
10. Angeli C A, Boakye M, Morton R A, Vogt J, Benton K, Chen Y, et al. Recovery of Over-Ground Walking after Chronic Motor Complete Spinal Cord Injury. N Engl J Med 2018; 379: 1244-1250.

The claims defining the invention are as follows:

1. A rehabilitation system for lower limb rehabilitation of a person with a neurological condition, the system including:
    exercise equipment for enabling the person to exercise using at least one lower limb;
    a human machine interface including one or more body sensors for sensing information from the person during exercise;
    one or more equipment sensors for sensing information of the exercise equipment; and
    a personalized computer model which is a neuromusculoskeletal model including a digital twin of the person exercising using the exercise equipment, wherein the personalized computer model is configured to;
        receive the sensed information from the one or more body sensors and from the one or more equipment sensors,
        generate electrical stimulation and actuation assistance for the person exercising with the exercise equipment using the at least one lower limb, and
        generate somatosensory data to be provided to the person through extended reality.

2. The rehabilitation system as claimed in claim 1, wherein the personalized computer model generates suitable electrical stimulation while avoiding-avoids excessive stresses on the person-which can lead to fracturing of bones.

3. The rehabilitation system as claimed in claim 1, wherein the one or more body sensors include biomechanical and/or physiological biosensors.

4. The rehabilitation system as claimed in claim 1, wherein the sensed information relates to one or more of electromyography, inertial measurement units, heart rate, electrocardiogram, and respiration.

5. The rehabilitation system as claimed in claim 1, wherein the one or more equipment sensors include speed or torque sensors.

6. The rehabilitation system as claimed in claim 1, wherein the somatosensory data is further provided via visual, auditory and/or haptic feedback.

7. The rehabilitation system as claimed in claim 1, wherein the personalized computer model is configured to receive the person's intention of movement data from a brain-computer interface.

8. The rehabilitation system as claimed in claim 7, wherein the human machine interface provides somatosensory feedback enabled by extended reality feedback, wherein the extended reality feedback includes a virtual or augmented reality headset with visual, auditory and/or tactile feedback.

9. The rehabilitation system as claimed in claim 1, wherein the one or more body sensors include wearable sensors configured to be worn by the person.

10. The rehabilitation system as claimed in claim 1, wherein the exercise equipment includes a recumbent ergometer.

11. The rehabilitation system as claimed in claim 1, further including an actuator for actuating the exercise equipment.

12. The rehabilitation system as claimed in claim 11, wherein the actuator includes a motor.

13. The rehabilitation system as claimed in claim 12, wherein the extended reality feedback includes virtual reality, tactile via haptic feedback, or auditory by ear phones.

14. A rehabilitation system for lower limb rehabilitation of a person with a neurological condition, the system including:

exercise equipment for enabling the person to exercise using at least one lower limb;

a human machine interface with one or more body sensors for sensing information from the person during exercise, the human machine interface being configured to provide somatosensory feedback enabled by extended reality feedback;

one or more equipment sensors for sensing information of the exercise equipment; and a personalized computer model which is a neuromusculoskeletal model including a digital twin of the person exercising using the exercise equipment, wherein the personalized computer model is configured to:
- receive the sensed information from the one or more body sensors and from the one or more equipment sensors,
- generate electrical stimulation and actuation assistance, assisted by actuators, for the person exercising with the exercise equipment using the at least one lower limb, and
- synthesize and generate somatosensory data to be provided to the person through the extended reality feedback.

15. A rehabilitation method for lower limb rehabilitation of a person with a neurological condition, the method including:

exercising the person with exercise equipment using at least one lower limb;

sensing information from the person exercising using one or more body sensors of a human machine interface;

sensing information of the exercise equipment using one or more equipment sensors; and providing a personalized computer model which is a neuromusculoskeletal model including a digital twin of the person exercising using the exercise equipment, wherein the personalized computer model is configured to:
- receive the sensed information from the exercising person and of the exercise equipment,
- generate electrical stimulation and actuation assistance for the person exercising with the exercise equipment using the at least one lower limb, and
- generate somatosensory data for provision to the person through extended reality.

16. The rehabilitation method as claimed in claim 15, wherein the personalized computer model generates suitable electrical stimulation while avoiding excessive stresses on the person which can lead to fracturing of bones.

17. The rehabilitation method as claimed in claim 15, wherein the sensing information from the exercising person includes one or more of somatosensory, visual feedback, tactile and auditory sensing.

18. The rehabilitation method as claimed in claim 15, further including actuating the exercise equipment.

* * * * *